United States Patent [19]

Miller

[11] Patent Number: 5,004,687

[45] Date of Patent: Apr. 2, 1991

[54] INSECT VIRUS VECTOR WITH BROADENED HOST RANGE

[75] Inventor: Lois K. Miller, Moscow, Id.

[73] Assignee: University of Georgia Research Foundation, Inc., Athens, Ga.

[21] Appl. No.: 736,478

[22] Filed: May 21, 1985

[51] Int. Cl.[5] ...................... C12N 15/86; C12N 15/00; C12N 7/01

[52] U.S. Cl. ................................ 435/69.1; 435/320.1; 435/235.1; 935/32; 935/57; 935/70; 935/36

[58] Field of Search ........................ 435/68, 91, 70, 13, 435/253, 317, 320; 935/11, 29, 34, 36, 56, 60

[56] References Cited

U.S. PATENT DOCUMENTS 4,745,051 5/1988 Smith et al. .......................... 435/68

FOREIGN PATENT DOCUMENTS 0127839 5/1984 European Pat. Off. .

OTHER PUBLICATIONS

McIntosh et al. (1980) Intervirology 13: 331-41.
Glutman (1982) in Eukaryotic Virol Vectors, Cold Spring Harbor, N.Y.
Gorman et al. (1982) FNAS 79: 6777-81.
Smith et al. (1983) Mol & Cell. Biol. 3: 2156-65.
Carter (1984) in "Biotechnology of Genetic Engineering Reviews", vol. I, ed. Russell, Intercept, Newcastle-upon-Tyne, pp. 375-419.
Science, vol. 219: 715-721 (1983).
Molecular and Cellular Biology, 4:339-486 (1984).
Molecular and Cellular Biology, 3:2156-2165 (1983).
Summers, et al., eds., "Baculoriruses for Insect Pest Control: Safety Considerations", American Society for Microbiology (1975).
Summers, et al., eds.; Viral Pesticides: "Present Knowledge and Potential Effects on Public and Environmental Health", U.S. EPA (1978).
McIntosh et al., Ann. NY Acad. Sci. 266: 327-331 (1975).
Granados, "Replication Phenomena of Insect Viruses", in Miltenburger at pp. 163-184 (1978).
Volkman et al., Appl. Environ. Microbiol. 45: 1085-93 (1983).
Tjia, Virol. 125: 107-117 (1983).
Himeno, Virol., 33: 507-5112 (1967).
McIntosh et al., Intervirol., 13:331-341 (1980).
Groner et al., Intervirol., 21:203-209 (1984).
Miller, Virol. 126: 376-380 (1983).
Kelly et al., Microbiologica 4:35-57 (1981).
Gordon et al., Virol. 138: 69-81 (1984).
Lee and Miller J. Virol. 31: 240-52 (1979).
Summers et al., J. Gen. Virol. 40: 545-57 (1978).
Gorman, et al., PNAS (USA) 79: 6777-81 (1982).
Sherman et al., Infection & Immun., 26: 232-234 (1979).

*Primary Examiner*—Richard A. Schwartz
*Assistant Examiner*—S. L. Nolan
*Attorney, Agent, or Firm*—Gregory D. Williams; Sewall P. Bronstein

[57] ABSTRACT

A novel viral expression vector is employed in the expression of exogenous genes in "non-permissive" hosts. Exogenous genes under the control of a promoter which promotes expression in "non-permissive" hosts are thus used to expand the host range of the virus thus allowing production of polypeptides, including polypeptides which are toxic to the target host.

8 Claims, 2 Drawing Sheets

INSECT VIRUS VECTOR WITH BROADENED HOST RANGE

This is a continuation-in-part of co-pending application Ser. No. 575,453, filed on Jan. 31, 1984.

BACKGROUND OF THE INVENTION

The present invention relates to methods and products thereof for expanding the host range of certain viruses, and more particularly to the expansion of a baculovirus' host range through the use of a promoter which is active in the target host. Viruses with expanded host range may be used to express exogenous genes in the target host and more specifically to produce polypeptides which are toxic to the host.

Interest in microbial insecticides has arisen as a result of the problems associated with the use of chemical pesticides. Chemical pesticides generally affect beneficial as well as non-beneficial species, and insects tend to acquire resistance to such chemicals so that new insect populations are resistant to the chemical pesticides. Moreover, pressures are brought to bear by environmentalists concerned about the effect of chemical pesticides on wildlife, by pest-control experts concerned about the effects of these pesticides on parasites and predators of the pests, by consumers concerned about toxic residues in food, and by public health officials concerned about human poisoning. Furthermore, research, development and production costs for chemical pesticides have soared, making them expensive in the developed nations, while in the developing nations, if pesticides are used at all, farmers select the least expensive, which are usually the most toxic.

Microorganisms (entomopathogens) present an opportunity for an alternative means of pest control and can play a role in integrated pest management thus reducing the dependence on chemical pesticides. Naturally occurring microorganisms or microbial by-products have been identified and found to be useful as insecticidal agents. A number of entomopathogens have relatively narrow host ranges, which has made it possible to reduce specific pest populations while natural predators and beneficial insects are preserved or given the opportunity to become reestablished. Entomopathogens which are useful for insect control include certain bacteria, viruses, and fungi.

Viruses that cause natural epizootic diseases within insect populations have been commercially developed as pesticides. One such family of viruses that has been extensively studied is the Baculoviridae. Baculoviruses posses large (about 100 to 200 kilobases), double-stranded, circular, covalently closed DNA genomes that are packaged in enveloped, rod-shaped capsids approximately 40 to 140 by 250 to 400 nanometers. The term "baculovirus" is derived from the rod-shaped nucleocapsid structure which is characteristic of this family. A nucleocapsid is a unit of viral structure, consisting of a capsid (protein coat) with an enclosed nucleic acid.

The nuclear polyhedrosis viruses and granulosis viruses baculovirus subgroups have been investigated for use as entomopathogens. The advantages of using viruses from the family Baculoviridae include: (1) they are known to cause lethal infections only in invertebrates; (2) they have a relatively specific host range; (3) they produce sufficient progeny virus per insect to allow commercial production; and (4) the virus particles of NPV and GV are occluded in proteinaceous crystals which renders the viruses more stable in the environment, increases the shelf life as commercially prepared microbial pesticides, and facilitates combination with other pesticide formulations.

When used as pesticides, occluded viruses are usually sprayed on foliage. Insects that consume the contaminated foliage acquire the virus-induced disease. The ingested virus passes through the foregut of the insect to the midgut where the alkaline pH solubilizes the crystal. The virions are released from the matrix and begin the infection of the midgut columnar cells by fusion with microvillar membrane. Upon the death of the insect and the disintegration of the integument, the occluded viruses are released into the surrounding environments, and, if consumed by susceptible hosts, spread the infection.

The most extensively studied baculovirus is the *Autographa californica* nuclear polyhedrosis virus (AcNPV) which has a relatively broad host range. The AcNPV DNA genome (128 Kilobases) has been mapped with respect to restriction sites for various restriction endonucleases, and is primarily composed of unique nucleotide sequences. See L. K. Miller et al., *Science* Vol. 219:715–721 (1983).

Nuclear polyhedrosis viruses, such as AcNPV, have a double-stranded circular DNA genome of 128 kb. The nucleocapsid is rod-shaped and found packaged in two forms, the non-occluded form, a membrane budded virus, and an occluded form, packaged in a protein crystal in the infected cell nucleus. These viruses can be routinely propagated in in vitro insect cell culture and are amenable to all routine animal virological methods. The cell culture media is typically a nutrient salt solution supplemented with 10% fetal calf serum.

In vitro, virus growth is initiated when a non-occluded virus (NOV) enters a cell and moves to the nucleus, where it replicates. During the initial phase of viral replication (8–18 hours post-infection), nucleocapsids are assembled in the nucleus and exported from the cell by budding through the plasma membrane. The resulting NOV cause the infection to spread through the cell culture. Then, some of the nucleocapsids subsequently (18+hours post-infection) remain in the nucleus and are occluded in a protein matrix, known as the polyhedral inclusion body (PIB). This form is not infectious in cell culture. The matrix is composed of a protein known as polyhedrin, MW 29 kd. Each PIB is approximately 1um in diameter, and there can be as many as 100 PIBs per nucleus. There is clearly a great deal of polyhedrin produced late in the infection cycle, as much as 25% of total cellular protein.

Because the PIB plays no role in the in vitro replication cycle, the polyhedrin gene can be deleted from the virus chromosome with no effect on in vitro viability. Recently, two groups have reported using the virus as an expression vector in permissive cells by replacing the polyhedrin gene coding region with the foreign DNA to be expressed and placing it under the control of the polyhedrin promoter. This results in a non-PIB forming virus phenotype. Pennock, et al., Molecular and Cellular Biology, 4:399–406 (March 1984), fused the N-terminal region of the gene encoding polyhedrin, the major occlusion protein of the insect baculovirus *Autographa californica* nuclear polyhedrosis virus to DNA encoding *Escherichia coli* B-galactosidase. The fused gene was inserted into the AcNPV DNA genome by co-transfection of insect cells with recombinant plasmid DNA and wild-type AcNPV genomic DNA which resulted in a recombinant virus expressing a fused gene product. Smith et al., Molecular and Cellular Biology, 3:2156–2165 (1983), linked the protein-coding sequences for interferon to the AcNPV promoter for the gene encoding for polyhedrin. The interferon gene was inserted at various locations relative to the AcNPV polyhedrin transcriptional and translational signals.

The host specificity of baculoviruses has been a subject of considerable discussion due to safety considerations with regard to their use as pesticides. (Summers, et al., eds. "Baculoviruses for insect pest control: Safety considerations." Washington, D.C.: American Society for Microbiology, 1975; Summers, et al., eds. Viral pesticides: "Present knowledge and potential effects on public and environmental health." Research Triangle Park, N.C.: U.S. Environmental Protection Agency, 1978). Very little, however, is known about the factors that control the host specificity of baculoviruses. AcNPV is considered to have a relatively broad host range for a baculovirus and is known to infect over 30 different species of Lepidoptera (J. B. Carter, 1984 "Viruses as Pest-Control Agents" in *Biotechnology and Genetic Engineering Review*, Volume I ed. G. E. Russell. Intercept, New Castle-upon-Tyne). Entry of the insect baculovirus AcNPV into non-permissive vertebrate cells is well-documented (McIntosh AH, et al., Ann NY Acad Sci 1975; 266:327–31; Granados, "Replication Phenomena of Insect Viruses in vivo and in vitro." In: Miltenburger HG, ed, Safety Aspects of Baculoviruses as Biological Pesticides. Bonn: Bundesministerium fur Forschung und Techologie, 1978:163–84; Volkman LE, et al., Appl Environ Microbiol 1983; 45:1085–93; and Tjia ST, zu Altenschildesche GM, et al., Virol. 125:107–17 (1983)). Although the replication of AcNPV in non-permissive invertebrate cells, i.e. dipteran and mammalian cells has been reported (Himeno M, et al., Virol. 33:507–12(1967); Sherman KE, et al., Infection and Immun., 26:232–4 (1979); and McIntosh AH, et al., Intervirol., 13:331–41 (1980)) the experimental methods and interpretations have been questioned by others (Groner A, et al., Intervirol., 21:203–9 (1984)). Following infection, it has been reported that at least some of the viral DNA apparently reaches the mammalian nucleus but does not persist and there is no evidence that baculovirus DNA is transcribed in mammalian cells (Tjia, zu Altenschildesche, et al., supra). Others have demonstrated that gene expression is not detectable following infection of either a dipteran or a mammalian cell line with a recombinant AcNPV containing an *E. coli-galactosidase* gene fusion under the control of a strong late promoter, the polyhedrin promoter where the B-galactosidase assay was sufficiently sensitive to have detected approximately 0.1% of the activity observed in permissive lepidopteran cells infected with the recombinant AcNPV (Pennock, et al., supra).

Although from an ecological or safety perspective, a pesticide with a rigorous host specificity is considered ideal for the protection of non-target organisms, from the perspective of commercial production and marketing, the ability of a single baculovirus to kill only a very limited number of insect species is often viewed as economically disadvantageous because of the need for large numbers of different products with limited applicability. There is, therefore, current industrial interest in expanding the host range of commercially produced baculoviruses to include other insect hosts while maintaining inherent advantages of baculoviruses, i.e. non-expression in mammalians.

SUMMARY OF THE INVENTION

In accordance with the present invention, the host range of a viral vector is for the first time expanded to include hosts in which the virus does not normally cause pathogenic effects. More specifically the present invention provides novel means of employing expression vectors, preferably an insect or entomopathogen virus expression vector, for expanding the host range of the virus to enable expression of a exogenous gene product in hosts not normally susceptible to viral pathogenesis. In a preferred embodiment, the present invention comprises cloning a region of an NPV (such as AcNPV), providing a plasmid which includes the gene region, inserting an exogenous gene under the control of a promoter which is active in non-permissive host cells into the gene region, co-transfecting the resulting passenger plasmid DNA with wild type AcNPV DNA into a host cell and use of the transformed host cell to produce a recombinant virus which can express the exogenous gene product in the desired host. One such promoter for use in connection with the present invention which allows expression of gene product in dipteran and other non-permissive cells is the long terminal repeat (LTR) of the Rous sarcoma virus (RSV). Other promoters which are active in unsusceptible host cells can also be used to produce exogenous gene products in insects which are normally not susceptible to the particular virus vector. Those promoters which are functional in such host cells may be identified by attaching the promoter to the gene encoding chloramphenicol acetyl transferase (CAT) and testing for enzymatic activity of the CAT gene product.

Thus, valuable host/vector systems are provided for introducing and expressing exogenous gene products in hosts which are otherwise not susceptible to pathogenic effects of the particular virus. The present invention therefore permits exogenous passenger DNAs, including those with gene products causing insect behavior changes, paralysis or death, to be introduced and expressed at high levels in insect orders which are normally refractive to infection by the virus, including Diptera, Coleoptera, Orthoptera, Isoptera, Hymenoptera and Thysanura.

BRIEF DESCRIPTION OF THE DRAWINGS

FIG. 1 shows the schematic construction of plasmid pLC-1

FIG. 2 shows expression levels of CAT and B-galactosidase in AcNPV LlLC-galcat-infected *S. frugiperda* cells.

FIG. 3 shows expression in AcNPV LlLC-galcat-infected *Drosophila melanogaster* cells.

DETAILED DESCRIPTION OF THE INVENTION

In accordance with the present invention, baculoviruses are provided which are useable a vectors for introducing and expressing exogenous DNA in non-permissive (i.e. normally refractive) hosts. More specifically, it has been found that a baculovirus is able to absorb, penetrate, uncoat and present its DNA in an expressible form to the transcriptional factors of insect cells of insects which are normally considered to be refractory to baculovirus infection. The ability of the baculovirus to mediate expression in non-permissive hosts is believed to be due to the type of promoter controlling gene transcription. Exogenous and endogenous promoters may be used as long as they promote expression in the non-permissive hosts. One such exogenous promoter which has been found to promote gene expression in non-permissive insect cells is the long terminal repeat of the Rous sarcoma virus (LTR-RSV). Although it has been found that this baculovirus containing LTR-RSV can also enter and express genes in mammalian cells, it does so much less efficiently.

The methods described herein by which the host range of a virus is expanded to include non permissive or refractory hosts include the steps of attaching the exogenous gene to be expressed, such as a gene whose gene product is toxic to the ultimate host, to a promoter which promotes expression in the ultimate host cell such as promoters from other viruses, bacteria, fungae, insects, mammals, etc. The promoter-gene combination is thereafter inserted into an appropriate "transplacement vector". Alternatively, the gene could be put into the "transplacement vector" and then the promoter attached. The transplacement vector is designed so as to permit allelic replacement of an appropriate region of viral DNA. The plasmid pGP-B6874/Sal (FIG. 1) is one such transplacement vector. This plasmid has a single Pst I site in a non-essential region of the plasmid. The promoter-gene combination can be inserted into this Pst I site. The resulting recombinant plasmid is co-transfected with wild type viral DNA and recombinants selected by an appropriate technique. In the case of pGP-B6874/Sal, the vector is designed so that a blue color is produced for recombinant viruses resulting from allelic replacement. As noted above, one example of an exogenous promoter is the long terminal repeat promoter of Rous sarcoma virus, an avian sarcoma virus which is widely available. This promoter (RSV-LTR) has been inserted into AcNPV and shown to direct the synthesis in permissive insect cells of an exogenous protein, such as the chloramphenicol acetyl transferase gene of E. coli (See my corresponding U.S. application No. 575,453, the disclosure of which is hereby incorporated by reference). Other exogenous promoters which may be used include LTR's of transposable elements, retroviruses and insect enhancer sequences. One advantage of the use of an exogenous promoter such as RSV-LTR is that the promoter is expressed in uninfected cells and is therefore activated at early as well as late times in the viral replication process. Early expression may be useful in some applications of genetic engineering of baculoviruses and/or insect cells, particularly with respect to the use of baculoviruses as biological pesticides. Promoters endogenous to baculoviruses which may be used include the immediate early (alpha) and delayed early (beta) gene promoters such as those found in the Hind 3-K region of AcNPV (Friesen and Miller, J. Virol.(1985)in press).

Figure 1:
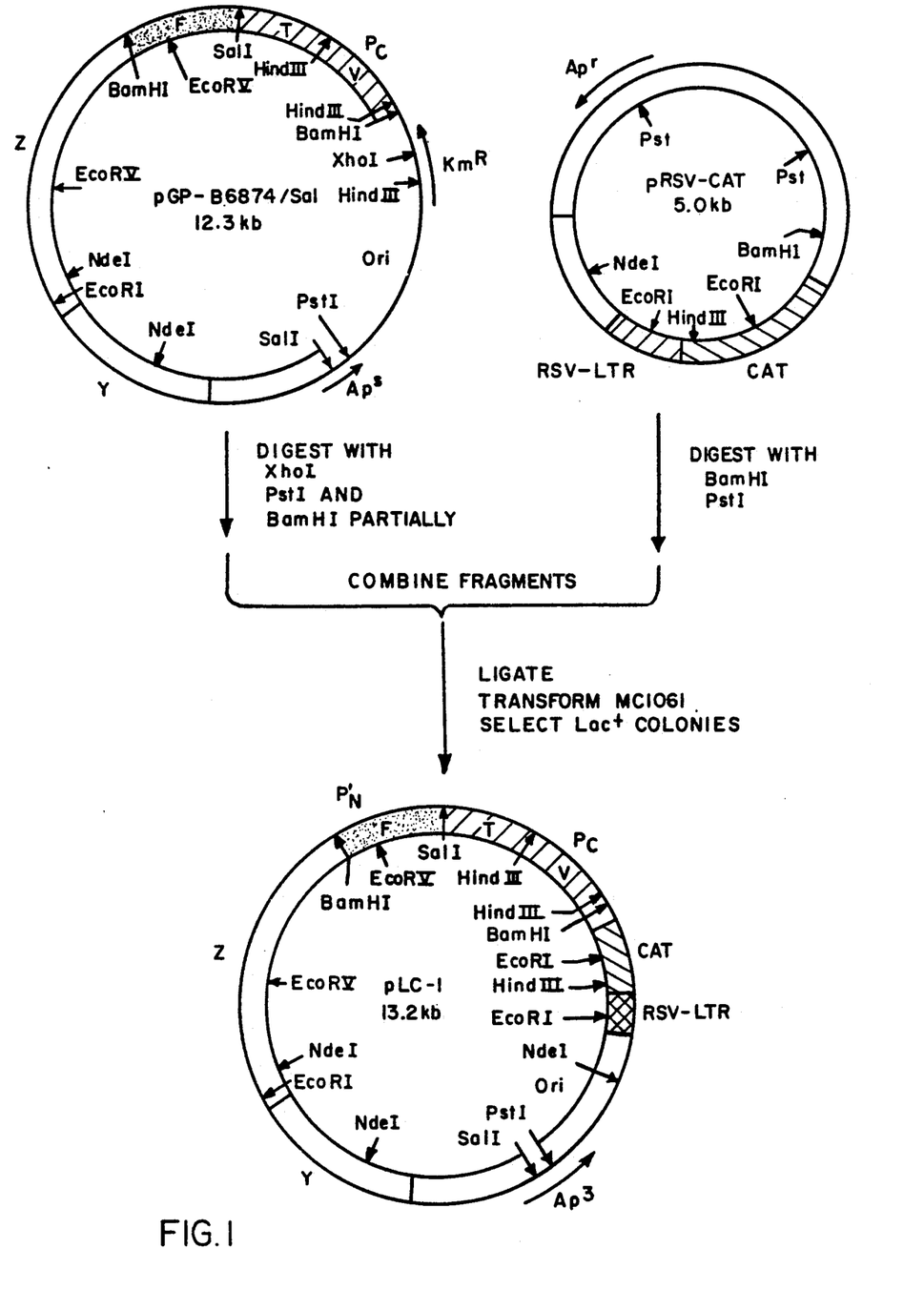

In accordance with another aspect of the present invention, there is provided a method for using such vector/host systems in non-permissive hosts. In a preferred embodiment, a recombinant virus, AcNPV L1LC-galcat, was constructed by allellic replacement of the nonessential wt polyhedrin gene with pLC-1 sequences (FIG. 1). AcNPV L1LC-galcat carries an approximatedly 10 Kb insert containing in order, the polyhedrin promoter, the polyhedrin N terminus fused in-frame with the E. coli B-galactosidase gene, the lac Y gene, part of the lac A gene, a portion of the B-lactamase gene, a col E1 origin for replication in E. coli, the RSV-LTR acting as a promoter for the CAT gene, and a polyadenylation signal from SV40 DNA followed by the C-terminal regions of the polyhedrin gene.

Figure 2:
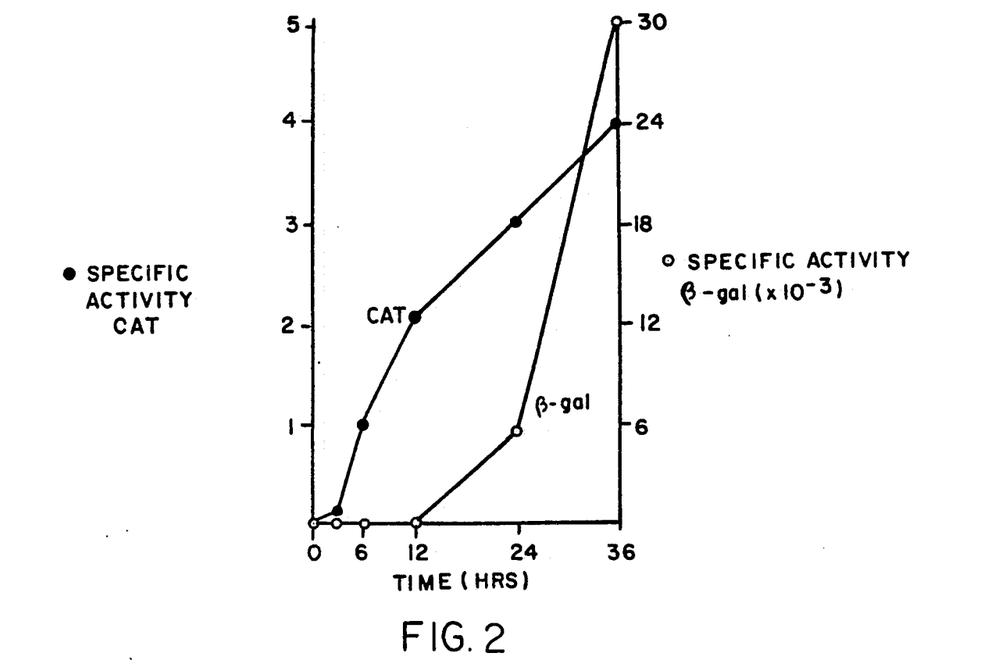

The temporal patterns of expression of the polyhedrin B-galactosidase fusion and CAT genes following inoculation of the permissive S.frugiperida IPLB-SF-21 cell line with AcNPV LILC-galcat were determined by assaying the enzymatic activities at various times post infection (p.i.) (FIG. 2). As expected from previous studies with AcNPV L1GP-ga13 (Pennock, et al., supra), the polyhedrin/B-galactosidase fusion gene under the control of the polyhedrin promoter was expressed as an occlusion-specific protein; B-galactosidase activity was not detected through 12 hours p.i. but was detected by twenty-four hours. Activity increased dramatically from twenty-four hours p.i. through thirty-six hours p.i. and represented an approximately 1,000 fold increase above the background levels observed at twelve hours p.i. In contrast, CAT activity was first observed at two hours p.i., increased substantially through twelve hours p.i., and then only doubled over the twenty-four hour period from twelve to thirty-six hours p.i.

The temporal pattern of expression of the two genes differed significantly. CAT gene expression was substantial even before the onset of extensive viral DNA synthesis (six hours p.i.); B-galactosidase expression was delayed until well after the onset of extracellular virus synthesis (beginning at ten to twelve hours p.i.) and coincided with the onset of occlusion, about twenty to twenty-four hours p.i. Relative to the levels of viral DNA in the cell (or copy number of the CAT gene), the greatest rates of CAT expression occurred between two and six hours p.i. Between six and eighteen hours, the number of CAT gene copies increased over 1,000 fold but CAT activity only doubled. The RSV-LTR may become less active with time, perhaps due to the depletion of host factors o template accessibility.

AcNPV L1LC-galcat-Mediated Gene Expression in Non-Permissive Drosophila Cells.

Previous studies of AcNPV-mediated gene expression in the *Drosophila melanogaster* DL-1 cell line employed AcNPV LIGP-ga13 as an inoculum and monitored B-galactosidase expression from the polyhedrin promoter; no B-galactosidase was detected in these studies (Pennock, et al., supra). Because the polyhedrin promoter is under strict temporal regulation, it was not clear from these studies if the lack of B-galactosidase expression was due to the failure of AcNPV DNA to enter the Drosophila nucleus or the failure of AcNPV to express late occlusion-specific genes in Drosophila cells.

Figure 3:
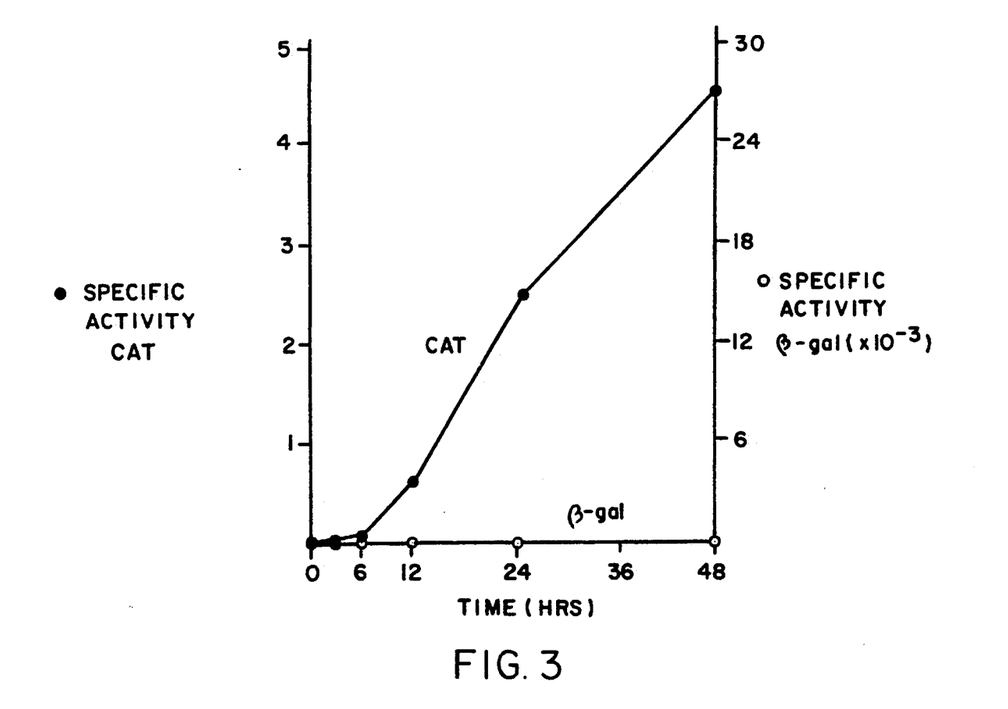

In accordance with the present invention, Drosophila cells were infected with AcNPV LILC-galcat and monitored for CAT and B-galactosidase gene expression. A mild cytopathic effect was noted in infected cells at twenty-four to forty-eight hours p.i. FIG. 3 shows that CAT expression was detected by six hours p.i., increased up to forty-eight hours p.i. after which it leveled off. The maximum specific activity observed was 4.5 nmol chloramphenicol acetylated per milligram per minute at 48 hours p.i. This value is approximately the same as the specific activity of CAT detected in infected *S. frugiperda* cells which are fully permissive. The results show that AcNPV is capable of absorbing, penetrating and uncoating in Drosophila cells so that the viral DNA is in an expressible form. B-galactosidase activity was not detectable in AcNPV L1LC-galcatinfected cells throughout the forty-eight hours monitored; the assay was sensitive enough to detect 0.3% of the activity in permissive cells. This indicates that gene expression in Drosophila cells is promoter-dependent.

AcNPV L1LC-galcat-Mediated Gene Expression in Midgut Cells of Mosquito Cells.

Positive CAT gene expression in Drosophila cells suggested that AcNPV-mediated gene expression could occur in a wide range of "non-permissive" insects. Since the midgut is the site of primary infection in insects, it was of practical significance to determine if midgut cells of an insect, that show no substantial signs of AcNPV infection, would sustain CAT gene expression upon AcNPV L1LC-galcat infection of the midgut. The experiment was also of interest since many promoters, including those of retroviruses, are tissue-specific in their expression.

To avoid questions concerning the amount of virus administered and its survival in food preparations or the insect foregut, the virus inoculum was introduced into the insect midgut. Adult female mosquitoes were inoculated with approximately $2 \times 10^7$ virus per midgut. After forty-eight hours p.i. in vivo. the midguts were removed from the mosquitoes and assayed for CAT activity and protein content. The specific activity at forty-eight hours p.i. was 2.3 nmoles chloramphenicol acetylated per milligram per min (Table I).

This result indicates that the extracellular form of AcNPV can absorb, penetrate and uncoat in the midgut cells of dipteran insects. Furthermore, the RSV-LTR is an active promoter in these specialized insect cells. The precise multiplicity of infection (m.o.i.) was not calculated in the mosquito midgut experiment but was roughly estimated that it is between 20 and 200 pfu/cell. The specific activity of CAT in mosquito midguts is in a similar range to that observed in Drosophila cell cultures (Table I).

TABLE I

| CELL TYPE | MOI | SPECIFIC ACTIVITY ACTIVITY OF CAT[a] |
|---|---|---|
| Spodoptera frugiperda cell line | 20 | 7.9 |
| Drosophila melanogaster cell line | 50 | 4.5 |
| | 500 | 4.2 |
| Aedes aegypti (UGAL) midgut cells | 20-200[b] | 2.3 |
| Mus musculus cell line | 800 | not detectable |
| | 800[c] | $1.5 \times 10^{-3}$ |

[a]Measured at 48 hrs. post-infection.
[b]Approximate moi $2 \times 10^7$ pfu per midgut delivered as an enema.
[c]Virus inoculum was allowed to remain in the media during incubation.

AcNPV L1LC-galcat-Mediated Gene Expression in Mammalian Cell Cultures

Observation of substantial CAT gene expression in dipteran cells raised the question of virus entry and gene expression in non-target mammalian cells. Two previous reports had failed to detect AcNPV gene expression in mammalian cells (Tjia ST, et al., supra; Pennock, et al., supra).

Inoculation of a mouse cell line (Mus musculus L929) with AcNPV L1LC-galcat at a m.o.i. of 800 failed to yield CAT gene expression. In these as well as the previous experiments in insect cells, the virus inoculum was withdrawn following the initial one hour adsorption period. If the virus inoculum was left on the cell monolayer during subsequent incubation, a low level of CAT actifity was detected. The maximum specific activity observed in mouse cell cultures was $1.5 \times 10^{-3}$ nmol chloramphenicol acetylated per min per mg at forty-eight hours p.i. By ninety-six hours p.i., the specific activity of CAT decreased to 70% of the forty-eight hour expression level (data not shown in Table I). The forty-eight hour maximum specific activity was less than 0.05% that observed in "non-permissive" dipteran cells at an equivalent m.o.i. (Table I). The results show that AcNPV can enter mammalian cells and express genes from a mammalian-active promoter (RSV-LTR) but there appears to be a barrier at some step in the penetration or uncoating process since the pRSVcat construct is known to be highly active in mouse cells by $CaCl_2$ transient expression assay (Gorman, et al., PNAS (USA) 79:6777-81 (1982)).

Persistence of AcNPV DNA in a Non-Permissive Insect Cell Line.

In an experiment designed to determine the persistence of CAT gene expression in AcNPV L1LC-galcat-infected Drosophila cells, infected cells were maintained for twenty-two days p.i. and CAT activity was assayed at various times p.i. Maximum CAT expression was observed at forty-eight hours p.i. and continued to decrease with time; by twenty-two days p.i., no CAT activity could be detected. In order to maintain the cells, it was necessary to split the cells one to eight every three days. The specific activity of CAT decreased at a rate that could be accounted for by cell multiplication, e.g. the specific activity decreased by approximately one-eighth every three days. The high specific activity of CAT in the infected Drosophila cells suggested that most cells acquired viral DNA. The decrease in CAT specific activity with time could be accounted for by the lack of viral DNA replication with cell division. Other explanations, however, are also possible.

Thus, it has been found in accordance with the present invention that RSV-LTR is a functional promoter in Drosophila and mosquito cells as well as in Lepidopteran cells. The late polyhedrin promoter, however is not detectably active in the "non-permissive" dipteran and mammalian cells. This appears to be due to the fact that polyhedrin expression is tightly regulated by other viral gene products. Polyhedrin synthesis occurs very late (eighteen hours p.i.) in the virus replication cycle and is dependent upon the expression of other viral gene products (Miller, L. K., et al., Vir. 126: 376-80 (1983); Kelly, et al., Microbiologica 4:35-57 (1981); and Gordon, et al., Vir. 138: 69-81 (1984)) and their activity may be dependent upon their interaction with host factors( Lee and Miller, J. Virol. 31:240-52 (1979); and Summers, et al., J. Gen. Virol. 40:545-57 (1978)). Other viral promoters, such as alpha (two hours), beta (six hours) or gamma (twelve hours) promoters (Friesen and Miller, J. Virol. (1985 in press)) may also drive CAT gene expression in non-permissive cells. In particular, it is likely that at least the alpha class of promoters will function in some of the"non-permissive" cells described above. A transient cytopathic effect in Drosophila cells was noted at twenty-four hours post-infection with AcNPV L1LC-galcat so that some viral promoters may be active. The nature of the promoter attached to a foreign toxin gene will thus be a controlling factor in the ability of the recombinant virus to affect a given host.

It is particularly significant from a perspective of pesticide use that the RSV-LTR is active in the midgut cells of insects since these cells are the site of primary infection. If the effective host range of a baculovirus is to be expanded to non-permissive hosts by introducing a toxin gene into the baculovirus genome, then it is important that the promoter controlling toxin gene expression is active in the midgut cells of the non-permissive targets. Expression of a highly toxic protein in the midgut could also increase the efficacy of viral pesticides in permissive insects, by accelerating the onset of morbidity or causing paralysis thereby blocking feeding.

The following examples are given to illustrate embodiments of the invention as it is presently preferred to practice it. It will be understood that these examples are illustrative, and the invention is not to be considered as restricted thereto except as indicated in the appended claims.

EXAMPLE I

Construction of a Transplacement Vector and its Use to Generate Plasmids for Expanding Host Range of Baculovirus.

In practicing the present invention, it is preferred to insert passenger genes under exogenous promoter control into the vector. In one such application, the transplacement vector plasmid pGP-B6874/Sal was constructed. This plasmid has been inserted in $E.$ $coli$ HB 101, a sample of which has been deposited at the American Type Culture Collection, and is held under ATCC accession number 39590. This vector provides a single Pst I site for the insertion of a passenger DNA under the control of its own or other exogenous promoter and allows the recombinant plasmid to be inserted into AcNPV using "blue" plaques as the means for selecting recombinant viruses.

The pGP-B6874/Sal plasmid illustrated in FIG. 1 was constructed by partially digesting pGP-B6874 with the restriction endonuclease Sal I and religating at low DNA concentration. Following transformation of $E.$ $coli$ HB 101, blue colonies were selected on kanamycin plates and then tested for sensitivity to ampicillin. The plasmids of $Amp^s$, $Kan^r$, blue colonies were characterized by restriction endonuclease analysis. The pGP-B6874/Sal plasmid was shown to contain the regions beta-gal including the lac Z (beta-galactosidase gene, "Z") lac Y, ("Y"), Rep and Kan ® genes to the Sal I site of Eco RI-I (S). The pGP-B6874/Sal plasmid is essentially pMC874 bordered by the N terminus and C terminus of the polyhedrin gene as in pGP-B6874. The Pst I site is not essential for beta-galactosidase expression or replication in $E.$ $coli.$ $E.$ $coli$ containing pGP-B6874/Sal are blue on x-gal plates and red on Maconkey plates.

Thus a transplacement plasmid, pGP-B6874/Sal has been constructed and may be used to facilitate the insertion and selection of recombinant viruses carrying passenger genes which are under the control of their own or exogenous promoters. Passenger genes can be inserted at the unique Pst I site next to the $E.$ $coli$ replication genes of the plasmid and cloned in $E.$ $coli.$ The co-transfection of the resulting plasmid with wild type AcNPV and subsequent selection for blue viruses, should facilitate the selection of recombinant viruses.

To demonstrate the utility of p-GP-B6874/Sal as a transplacement vector and to demonstrate the effective use of an exogenous promoter which permits expansion of a baculovirus host range, the $E.$ $coli$ gene encoding chloramphenicol acetyl transferase (CAT) attached to the exogenous promoter, RSV-LTR, was inserted into p-GP-B6874/Sal. The scheme for this construction is found in FIG. 1. The plasmid pRSV-CAT (Gorman et al, Proc Natl Acad Sci. 79:6777–81 (1982)) was digested with PstI and BamHI. The transplacement plasmid pGP-B6874/Sal was digested with PstI and partially digested with BamHI. The two restriction endonuclease-digested plasmids were mixed and ligated. The resulting recombinant plasmids were introduced into $E.$ $coli$ by transformation and lac+ colonies were selected on minimal media. The plasmid pLC-1 (See FIG. 1) was isolated and its structure verified by restriction endonuclease analysis. This plasmid has been inserted in $E.$ $coli$ MC1061, a sample of which has been deposited at the American Type Culture Collection, and is held under ATCC 53126 accession number.

More specifically, plasmid p-GPB6874/Sal DNA was digested with XhoI and PstI to completion and with BamHI partially so that the small PstI-BamHI fragment containing the origin of replication in $E.$ $coli$ (ori) and Km ® gene would be detached from the bulk of the plasmid DNA and further broken at the XhoI site. This PstI-BamHI region of p-GPB6874/Sal was replaced with a PstI-BamHI fragment from pRSVcat containing an $E.$ $coli$ replication origin (ori), the CAT gene under the control of the Rous Sarcoma Virus long terminal repeat (RSV-LTR) promoter, and a portion of the B-lactamase gene ($Ap^S$). Following ligation with T4 DNA ligase (Maniatis, et al., "Molecular Cloning: A Laboratory Manual", Cold Spring Harbor, N.Y. (1982)) and transformation into $E.$ $coli$ MC1061 [(lacI POZYA) 74, gal U, gal K, $strA^r$, $hsdR^-$, (ara, leu)](Casabadan, et al., J. Mol. Biol., 138:179–207 (1980)), the appropriate ligation product, pLC-1, was selected on minimal agar plates (Miller, J. H. "Experiments in Molecular Genetics" Cold Spring Harbor, N.Y. (1972)) containing 0.2% lactose, 40 ug/ml leucine, and 50 ug/ml of X-gal thus selecting for lactose utilizing colonies. Further tests also showed that pLC-1 conferred resistance to chloramphenicol but this property was not used in the original selection for pLC-1. The physical nature of pLC-1 DNA was confirmed by restriction endonuclease analysis with BamHI, Pst I, Sal I, Hind III and EcoRI.

EXAMPLE II

Construction of a Recombinant AcNPV Containing pLC-1.

A recombinant AcNPV L1GP-gal3, containing a polyhedrin-B-galactosidase fusion gene under the control of the polyhedrin promoter was described previously (Pennock, et al., supra). A new recombinant virus, AcNPV L1LC-galcat was constructed by allelic replacement (marker rescue) of the polyhedrin gene of AcNPV L-1 with DNA sequences from the plasmid pLC-1 shown in FIG. 1. The procedure for allelic replacement with pLC-1 was similar to that described for AcNPV LIGP-gal3 construction (Penncock, et al., supra). Briefly, wild-type virus and plasmid DNA were co-transfected into $Spodoptera$ $frugiperda$ cells, the cells were overlaid with complete TC 100 media (Gibco) containing agarose and a B-galactosidase indicator, 5-bromo-4-chloro-3- indolyl-B-D- galactopyranoside (X-gal). Plaques of recombinant viruses were selected by their blue color in the agarose overlay and each plaque was directly replaque-purified on $Spodoptera$ $frugiperda$ cells. The second plaque purification involved a selection for plaques with a blue color but lacking polyhedra (occlusion bodies) in the infected centers. Blue, polyhedra-negative plaques were selected, virus stocks were produced and the viral DNA was screened by restriction endonuclease analysis using BamHI, PstI, Hind III, and EcoRI to ensure that the recombinant virus contained all the sequences of pLC-1 between the polyhedrin amino and carboxyl termini and lacked an intact polyhedrin gene.

EXAMPLE III

Infection of Non-Permissive Insect Host Cells with AcNPV L1LC-galcat.

Infection of mosquito midguts: Virus was introduced into the midguts of adult female *Aedes aegypti* (UGAL strain), 3 days post-emergence, via the anus using a micropipette (Klowden, Trans. Royal Soc. Trop. Med. Hyg. 75:354–8 (1981)). Thirty females were used per virus inoculum; each female received 4 ul of the virus preparation. The AcNPV L1LC-galcat preparation was $4.9 \times 10^9$ pfu/ml (blue plaques on X-gal plates), and AcNPV L1 was $8.0 \times 10^9$ pfu/ml; the virus inocula were suspended in Drosophila tissue culture media. Inoculated mosquitoes were maintained at 27° C. on a 10% sucrose diet in double containment cages especially designed for retaining recombinant DNA virus-infected mosquitoes. Forty-eight hours post-enema, the mosquitoes were chilled to 4° C., the midguts were removed by dissection and placed in 50 ul of 0.25 M Tris-HCl pH 7.8. Extracts were made from 28 midguts of AcNPV L1 inoculated females and from 28 midguts of AcNPV L1LC-galcat inoculated females. The extracts were prepared and assayed for B-galactosidase, CAT, and protein as described below. The results are illustrated in Table I, supra.

EXAMPLE IV

Infection of Mammalian Cells with AcNPV L1LC-galcat.

Virus inoculum was grown in *S. frugiperda* cells, pelleted and resuspended in RPMI-1640 media (Gibco) containing 13% fetal bovine serum and antibiotics. Monolayers of mouse L929 (Sandford, et al., J. Nat. Cancer Inst. 9:229–46 (1948)) cells were infected at an m.o.i. of 800 at room temperature for one hour. In some cases, the inoculum was removed after the one hour absorption period. Fresh media was added and the cells were incubated at 37° C. in an atmosphere containing 5% $CO_2$. Cells were collected at twelve, twenty-four, forty-eight and ninety-six hours p.i., washed with PBS (Lee and Miller, supra), pelleted and frozen in liquid $N_2$. Enzyme assays were performed as described below. The results are illustrated in Table I, supra.

EXAMPLE V

Enzyme and Protein Assays.

Cells were washed with phosphate buffered saline (Lee and Miller, supra) and scraped from plates with a rubber policeman in 1 ml of PBS. The cells were pelleted at $200 \times g$ for 10 minutes in Eppendorf tubes, washed with 1 ml PBS, frozen in liquid $N_2$, and stored at $-20°$ C. until assayed. For the assays, cells were suspended in 0.25 M Tris HCl, pH7.8 and disrupted by freeze-thawing in dry-ice/ethanol three times at five minute intervals. The cell debris was pelleted by centrifugation at $12,000 \times g$ for 10 minutes and the supernatant was assayed for B-galactosidase (Pennock, et al. supra,) and CAT activities (Gorman, et al., supra). Fifty or one hundred nCi (1 or 2 nmol) of $^{14}C$-chloramphenicol was used per CAT assay. The amount of acetylated material was quantitated by excising the regions of the thin layer support and counting the radioisotopes by liquid scintillation. For accurate quantitation of CAT levels, cell extracts were diluted so that 30% or less of the input chloramphenicol was acetylated. B-galatosidase levels are reported in Miller units (nanomoles of ONPG cleaved per minute per milligram of protein) and CAT levels are reported as nanomoles of chloramphenicol acetylated per minute per milligram of protein. Protein was quantitated using a protein assay (BioRad) based on the Bradford method (Bradford, Anal. Biochem. 72:248–54 (1976)).

What is claimed is:

1. A baculoviral vector for the production of an exogenous gene product in insect host cells wherein said host cells are incapable of permitting replication of an unmodified baculovirus which comprises an exogenous DNA sequence encoding the gene product wherein transcription of said DNA sequence is controlled by a promoter of an LTR selected from the group consisting of retroviral LTRs and transposable element LTRs.

2. The vector of claim 1, wherein the baculoviral vector comprises a nuclear polyhedrosis virus.

3. The vector of claim 2, wherein the nuclear polyhedrosis virus comprises an *Autographa californica* virus or variant thereof.

4. The vector of claim 3, wherein the vector comprises the plasmid pLC-1.

5. A method for producing an exogenous gene product in insect cells which method comprises culturing insect cells which are incapable of permitting replication of an unmodified baculovirus which cells have been infected or transfected with a recombinant baculoviral expression vector which comprises a gene coding for the exogenous gene product wherein transcription of said gene is controlled by a promoter of an LTR selected from the group consisting of retroviral LTRs and transposable element LTRs.

6. The method of claim 5, wherein the baculoviral vector comprises a nuclear polyhedrosis virus.

7. The method of claim 6, wherein the nuclear polyhedrosis virus comprises an *Autographa californica* virus or variant thereof.

8. The method of claim 7, wherein the vector comprises the plasmid pLC-1.

* * * * *

UNITED STATES PATENT AND TRADEMARK OFFICE
CERTIFICATE OF CORRECTION

PATENT NO. : 5,004,687

DATED : April 2, 1991

INVENTOR(S) : Lois Miller

Page 1 of 3

It is certified that error appears in the above-indentified patent and that said Letters Patent is hereby corrected as shown below:

On Title page, under "OTHER PUBLICATIONS" line 9, insert --Miller et al.-- before "Science".

Title page, "OTHER PUBLICATIONS" line 10, insert --Pennock et al.-- before "Molecular".

Title page, "OTHER PUBLICATIONS" line 12, delete "Baculoriruses" and insert --Baculoviruses--.

Title page, "OTHER PUBLICATIONS" line 24, insert --et al.-- after "Tjia".

Title page, "OTHER PUBLICATIONS" line 25, insert --et al.-- after "Himeno".

Title page, "OTHER PUBLICATIONS" line 28, insert --et al.-- after "Miller".

Column 4, line 49, delete "B" and insert --β--.

Column 5, line 15, delete "fungae" and insert --fungi--.

Column 5, lines 65 and 66, delete "B" and insert --β--.

Column 6, lines 4, 10, 12 and 26, delete "B" and insert --β--.

Column 6, lines 44, 45, 48, 55 and 67 delete "B" and insert --β--.

UNITED STATES PATENT AND TRADEMARK OFFICE
CERTIFICATE OF CORRECTION

PATENT NO. : 5,004,687

DATED : April 2, 1991

INVENTOR(S) : Lois Miller

Page 2 of 3

It is certified that error appears in the above-indentified patent and that said Letters Patent is hereby corrected as shown below:

Title page, "OTHER PUBLICATIONS" line 1, delete "McIntosh et al. (1980) Intervirology 13:331-41."

Title page, "OTHER PUBLICATIONS" line 2, delete "Glutman" and insert --Gluzman-- and change "Virol" to --Viral--.

Title page, "OTHER PUBLICATIONS" line 4, delete "Gorman et al. (1982) FNAS 79:6771-81".

Title page, "OTHER PUBLICATIONS" line 5, delete "Smith et al. (1983) Mol & Cell. Biol. 3:2156-65".

Column 1 line 52, delete "posses" and insert --possess--.

Column 4, line 58, delete "a" and insert --as--.

Column 5, line 55, change "(1985 in press)" to --Vol. 54 No. 2, 392-400 (May 1985)--.

Column 6, line 37, delete "o" and insert --or--.

Column 7, line 24, after in vivo delete "." and insert --,--.

Column 8, line 57, change "(1985 in press)" to --Vol. 54 No. 2, 392-400 (May 1985)--.

UNITED STATES PATENT AND TRADEMARK OFFICE
CERTIFICATE OF CORRECTION

PATENT NO. : 5,004,687
DATED : April 2, 1991
INVENTOR(S) : Lois Miller

It is certified that error appears in the above-indentified patent and that said Letters Patent is hereby corrected as shown below:

Column 10, line 28, delete "B" and insert --β--.

Column 10, line 58, delete "Penncock" and insert --Pennock--.

Col. 10, lines 62 and 63 delete "B" and insert --β--.

Column 11, line 32, delete "B" and insert --β--.

Column 12, line 17, delete "B" and insert --β--.

Signed and Sealed this

Twenty-fourth Day of August, 1993

*Attest:*

BRUCE LEHMAN

*Attesting Officer*  *Commissioner of Patents and Trademarks*